(12) United States Patent
Biedermann et al.

(10) Patent No.: US 8,361,118 B2
(45) Date of Patent: Jan. 29, 2013

(54) ELONGATED IMPLANT DEVICE AND BONE STABILIZATION DEVICE INCLUDING THE SAME

(75) Inventors: Lutz Biedermann, VS-Villingen (DE); Jürgen Harms, Karlsruhe (DE); Wilfried Matthis, Weisweil (DE); Detlev Ganter, Villingen-Schwenningen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 310 days.

(21) Appl. No.: 12/573,733

(22) Filed: Oct. 5, 2009

(65) Prior Publication Data

US 2010/0087862 A1  Apr. 8, 2010

Related U.S. Application Data

(60) Provisional application No. 61/103,861, filed on Oct. 8, 2008.

(30) Foreign Application Priority Data

Oct. 8, 2008  (EP) ..................................... 08017645

(51) Int. Cl.
*A61B 17/70* (2006.01)
(52) U.S. Cl. ........................................ 606/259; 606/257
(58) Field of Classification Search .......... 606/246–264, 606/278–279, 57
See application file for complete search history.

(56) References Cited

U.S. PATENT DOCUMENTS

| | | | | |
|---|---|---|---|---|
| 5,375,823 A | * | 12/1994 | Navas | 623/17.15 |
| 5,672,175 A | | 9/1997 | Martin | |
| 6,267,764 B1 | * | 7/2001 | Elberg | 606/255 |
| 7,621,940 B2 | * | 11/2009 | Harms et al. | 606/257 |
| 7,854,752 B2 | * | 12/2010 | Colleran et al. | 606/279 |
| 7,988,710 B2 | * | 8/2011 | Jahng et al. | 606/254 |
| 8,025,680 B2 | * | 9/2011 | Hayes et al. | 606/257 |
| 2002/0095154 A1 | * | 7/2002 | Atkinson et al. | 606/61 |
| 2003/0220643 A1 | * | 11/2003 | Ferree | 606/61 |
| 2004/0049190 A1 | | 3/2004 | Biedermann et al. | |

(Continued)

FOREIGN PATENT DOCUMENTS

| EP | 1 388 323 A1 | 2/2004 |
|---|---|---|
| EP | 1 757 243 A1 | 2/2007 |

(Continued)

OTHER PUBLICATIONS

European Search Report for European Application No. 08017645.6, Applicant, Biedermann Motech GmbH, European Search Report dated Jan. 22, 2009 and mailed Feb. 6, 2009 (7 pgs.).

*Primary Examiner* — Alvin Stewart
*Assistant Examiner* — Jacqueline Johanas
(74) *Attorney, Agent, or Firm* — Christie, Parker & Hale, LLP

(57) ABSTRACT

An elongated implant device for stabilizing the spinal column includes a rod-shaped member having a first end and a second end, the rod-shaped member defining a longitudinal axis of the implant device, a sleeve which is slidably arranged on the rod-shaped member, the sleeve having a free end and a coupled end, the coupled end being connected with an axial dampening element, and the axial dampening element, which is connected between the sleeve and the second end of the rod-shaped member to damp a movement of the sleeve along the longitudinal axis. The first end of the rod-shaped member may be configured to be connected to a first bone anchor and the sleeve may be configured to be connected to a second bone anchor.

22 Claims, 6 Drawing Sheets

U.S. PATENT DOCUMENTS

| | | | |
|---|---|---|---|
| 2005/0049708 A1* | 3/2005 | Atkinson et al. | 623/17.16 |
| 2005/0182400 A1* | 8/2005 | White | 606/61 |
| 2005/0203519 A1 | 9/2005 | Harms et al. | |
| 2005/0261682 A1* | 11/2005 | Ferree | 606/61 |
| 2005/0288670 A1* | 12/2005 | Panjabi et al. | 606/61 |
| 2006/0036240 A1 | 2/2006 | Colleran et al. | |
| 2006/0084987 A1* | 4/2006 | Kim | 606/61 |
| 2006/0189984 A1* | 8/2006 | Fallin et al. | 606/61 |
| 2006/0247635 A1* | 11/2006 | Gordon et al. | 606/61 |
| 2007/0043356 A1* | 2/2007 | Timm et al. | 606/61 |
| 2007/0203446 A1* | 8/2007 | Biedermann et al. | 604/11 |
| 2007/0276380 A1 | 11/2007 | Jahng et al. | |
| 2008/0039843 A1* | 2/2008 | Abdou | 606/61 |
| 2008/0097441 A1* | 4/2008 | Hayes et al. | 606/64 |
| 2008/0183213 A1* | 7/2008 | Veldman et al. | 606/257 |
| 2008/0234746 A1 | 9/2008 | Jahng et al. | |
| 2008/0300633 A1* | 12/2008 | Jackson | 606/257 |
| 2008/0319482 A1* | 12/2008 | Jackson | 606/246 |
| 2009/0105820 A1* | 4/2009 | Jackson | 623/17.11 |
| 2009/0105829 A1* | 4/2009 | Gimbel et al. | 623/17.16 |
| 2009/0131981 A1* | 5/2009 | White | 606/246 |
| 2009/0149885 A1* | 6/2009 | Durward et al. | 606/246 |
| 2009/0234388 A1* | 9/2009 | Patterson et al. | 606/246 |

FOREIGN PATENT DOCUMENTS

| | | |
|---|---|---|
| EP | 1 774 919 A1 | 4/2007 |
| WO | WO 2007/124249 A1 | 11/2007 |
| WO | WO 2008/021319 A2 | 2/2008 |

* cited by examiner

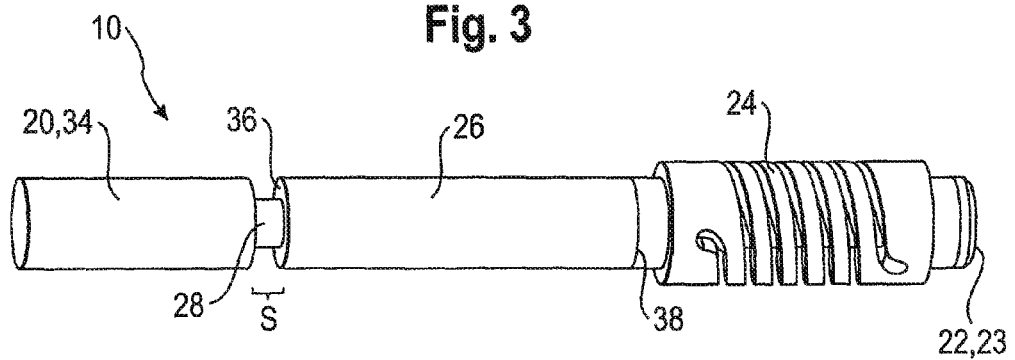
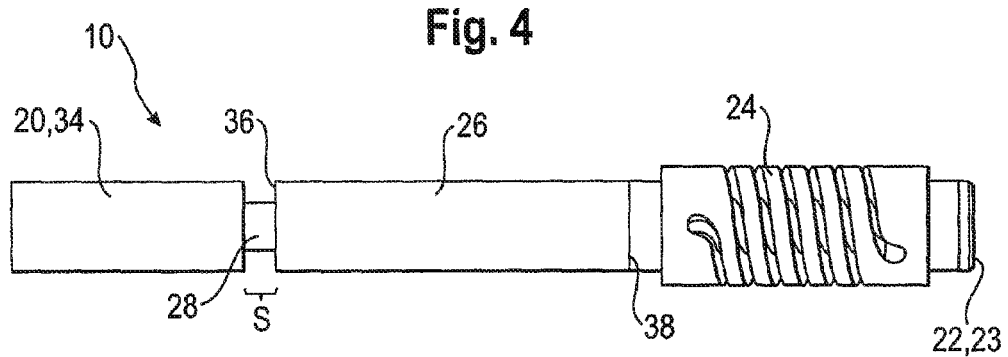
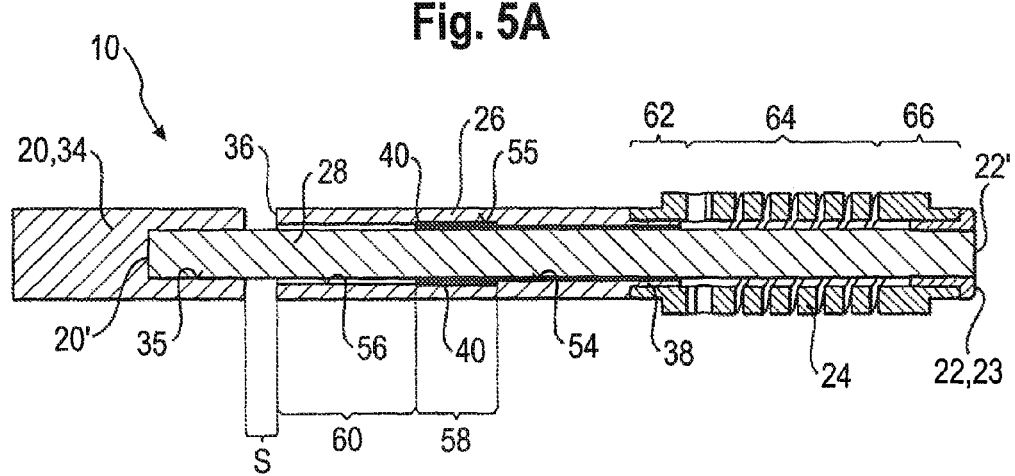

ELONGATED IMPLANT DEVICE AND BONE STABILIZATION DEVICE INCLUDING THE SAME

CROSS-REFERENCE TO RELATED APPLICATION(S)

The present application claims the benefit of U.S. Provisional Patent Application Ser. No. 61/103,861, filed Oct. 8, 2008, the contents of which are hereby incorporated by reference in their entirety, and claims priority from European Patent Application EP 08 017 645.6, filed Oct. 8, 2008, the contents of which are hereby incorporated by reference in their entirety.

BACKGROUND

The present application relates to an elongated implant device and bone stabilization device.

Bone anchors which are respectively inserted into adjacent human vertebrae may be connected to the implant device, in particular to the slidable sleeve and the first end of the rod-shaped member in order to stabilize the vertebral column. Since the sleeve is arranged to be slidable with respect to the first end of the rod-shaped member, some degree of flexion or torsion between vertebrae of the vertebral column can be maintained. Moreover, the dampening element may absorb shocks and relieves and/or distributes the load acting on the vertebrae participating in the bone stabilization.

An example of such a device is known from US 2007/0276, 380 A1. A connection unit of an implant device has a first end and a second end. A flexible element extends between the first and the second end, where a cap is attached. A spacer extends between the first end and the cap at the second end. The spacer has a central ring element and, on either side thereof, a resilient spring element. Thereby, the spacer is formed in a sleeve-like fashion such that the flexible element is lead through the spacer, which is thus guided by flexible element. A bone anchor may then each be connected to the first end and the ring element, such that—by means of both resilient spring elements—the ring element may be displaced from a rest position along the longitudinal axis of the flexible element, when forces are exerted on respective bone anchors.

The major forces act in tension or compression along the rod axis. In addition there are secondary loading components, which are bending, shearing and torsional loads. The inner flexible element is mostly acting against such secondary loads. This results in a major bending zone in between the two bone anchors. Such bending is directly transferred onto the flexible spring element, which is arranged between the ring element and the first end.

While the above described flexion does not imply problems with regard to the durability of the resilient spring element arranged between the bone anchors, which may also be valid in the case of torsion, a distinct perspective has to be attained with regard to shear, when material long-term fatigue after several millions of cycles is key.

Therefore, material fatigue of dampening elements, such as resilient spring elements, which are mainly intended to serve for dampening or absorbing forces acting in the longitudinal direction of an implant device, due, e.g., shear stress occurring between adjacent bone anchors should be prevented.

Further, mutual distances between adjacent bone anchors in an implant should be kept small and the resulting degree of flexion of the flexible element should be kept in a limited range.

SUMMARY

According to one aspect, an elongated implant device comprises a rod-shaped member, a sleeve which is slidably arranged on the rod-shaped member, and an axial dampening element. The axial dampening element serves to damp forces or shocks along the longitudinal axis of the rod-shaped member. The sleeve has one end which is free, i.e., it is not coupled with another member except elements which merely expand the sleeve body along the longitudinal axis. Hence, no resilient force acts on the free end of the sleeve. On the opposite side, the sleeve also has a coupled end, by which it is coupled with the axial dampening element. The axial dampening element is also connected with a second end of the rod-shaped member. As a result, the sleeve is supported with axial elasticity at the second end of the rod shaped member.

The first end of the rod-shaped member opposite to the second end has no connection with the sleeve except via the second end. In particular, due to the free end of the sleeve, which is oriented towards the first end, there is no dampening means directly between the first end of the rod shaped member and the sleeve.

The first end of the rod-shaped member and the sleeve are configured to be connected to a first and second bone anchor, respectively. The bone anchors and the elongated implant device act as a bone stabilization device. Forces acting on the two bone anchors may lead to compressing, tension, bending, shearing and torsional loads inside the elongated implant device. These forces are mostly acting between the two bone anchors. Especially bending and shearing loads are transferred by the rod-shaped member within a range between the free end of sleeve and the first end of the rod shaped member.

The single-sided elastic sleeve design results in additional bending, shearing forces through the axial dampening element. Hence, a location outside the major loading zone between the two bone anchors is advantageous. The outside location of the axial dampening element helps to improve fatigue life.

Further, since the axial dampening acting between the two bone anchors is concentrated outside of the inner range between both anchors, the mutual distance of the same may be decreased.

An elastic end stop may be optionally arranged at the free end to minimize high contact pressure. Such an element would not be contacted by the first end in an initial stage, but in cases of extraordinarily large forces acting onto the sleeve. So this element serves as a smooth end-stop in spinal extension movements.

The aspects described above will be better understood with reference to the description of following specific embodiment taken in conjunction with the accompanying drawings.

BRIEF DESCRIPTION OF THE DRAWINGS

FIG. 3 shows a perspective view of the elongated implant device shown in FIG. 1;

FIG. 4 shows a side view of the elongated implant device shown in FIG. 3;

FIG. 5A shows a sectional profile of the elongated implant device shown in FIG. 3;

DETAILED DESCRIPTION

Figure 1:
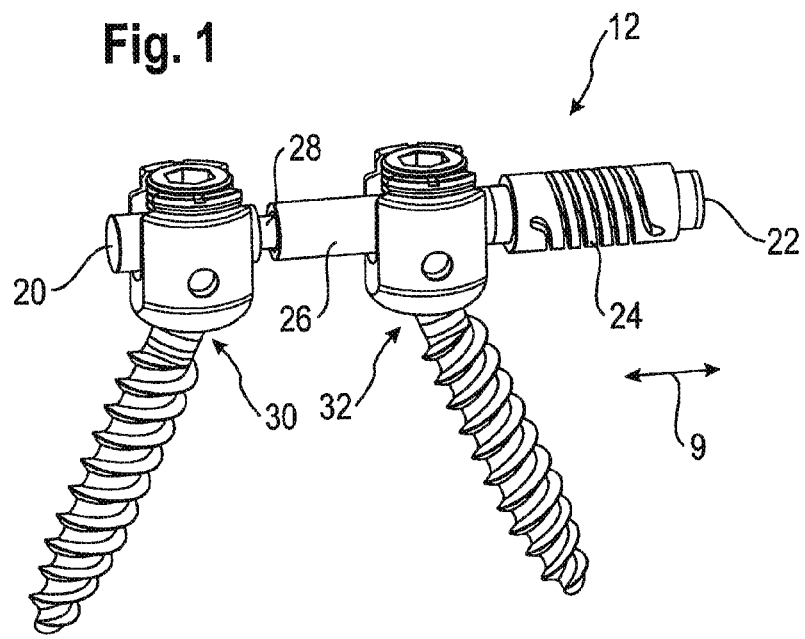
FIG. 1 shows a perspective view of a bone stabilization device including an implant device according to an embodiment of the invention.
Figure 2:
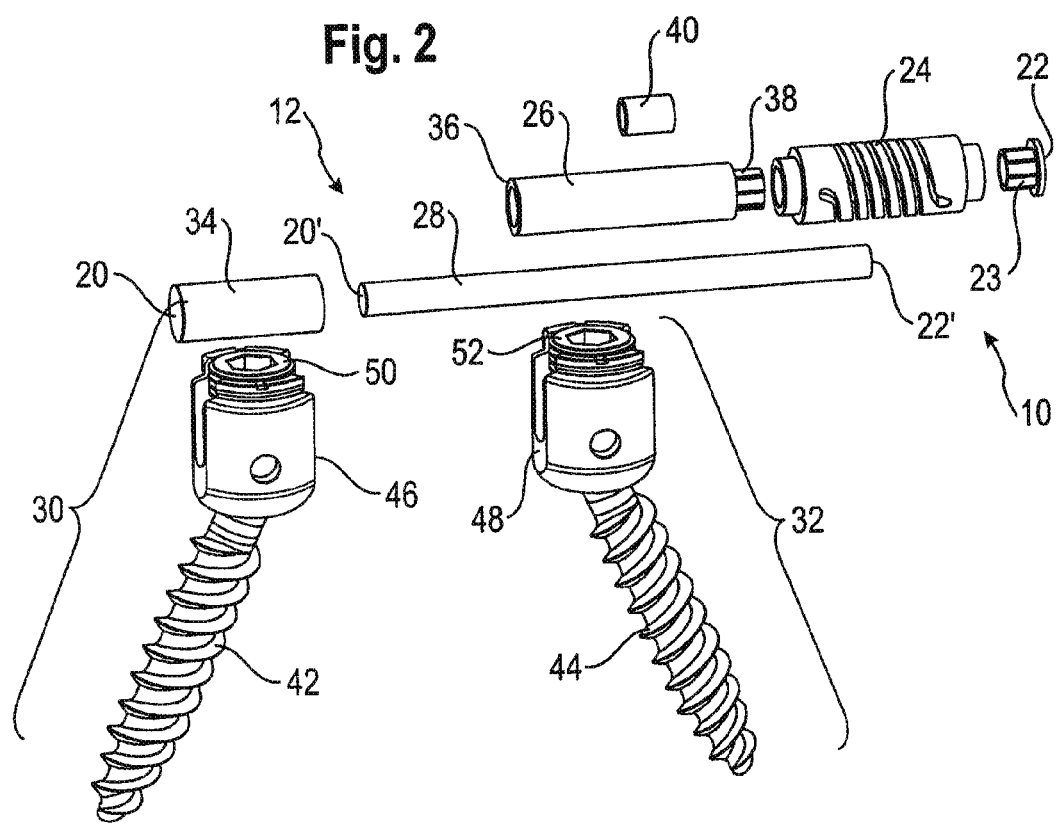
FIG. 2 shows an exploded view of the bone stabilization device of FIG. 1.
Figure 5B:
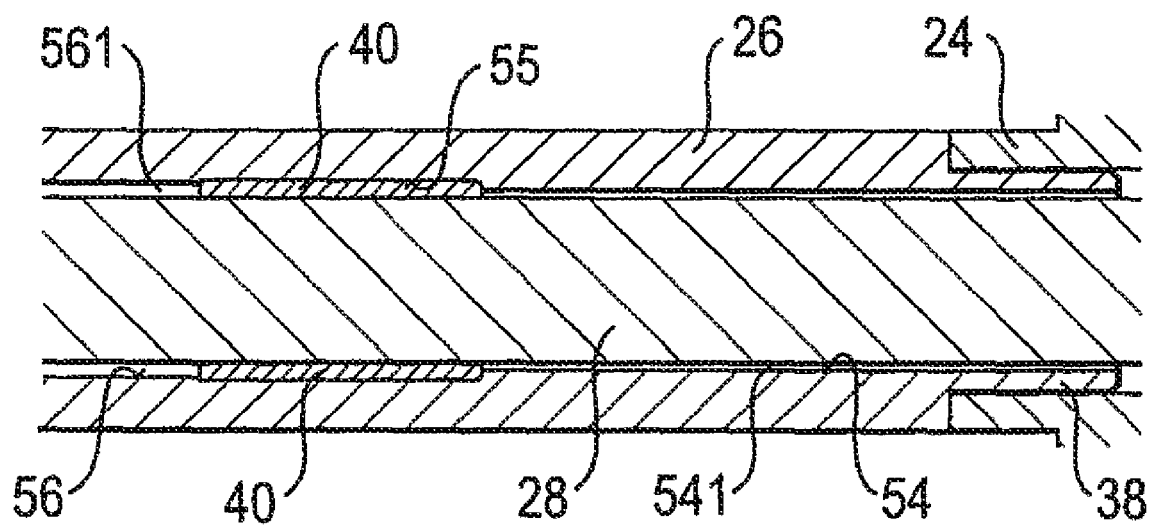
FIG. 5B shows the sectional profile of FIG. 5A in enlarged detail.

A specific embodiment of a bone stabilization device 12 is shown in FIGS. 1-8. FIG. 1 illustrates a perspective view, and FIG. 2 shows a corresponding exploded view showing more details of the implant device 10. The bone stabilization device includes two bone anchors 30, 32 and the implant device 10, which serves as a connection unit for the two bone anchors. The bone anchors 30, 32 are designed to be inserted into respective vertebrae of the human spinal column, for example. One key feature that may be seen from these Figures relates to the axial dampening element intended to damp relative motions between the two bone anchors, which is located outside a range of the implant between both anchors. More precisely, it may be located at an end position of the elongated implant device. A detailed description of the individual parts of the device is provided first:

The elongated implant device 10 includes a rod-shaped member 28, which may be formed as a flexible core, in particular as a thin flexible Nitinol wire and which can provide a desired bending and torsional elasticity of the implant device. The rod-shaped member 28 is not limited to the specific material noted above and may alternatively be formed from any other flexible biocompatible material which is known in the art of manufacturing surgery devices.

The rod-shaped member 28 is formed as a cylindrical rod of substantially constant diameter in this embodiment and has two ends 20', 22'. The first end 20' is inserted and rigidly fixed (e.g., press-fitted) within a bore 35 of a rod portion 34, which thus expands the rod shaped member 28 along its longitudinal axis thereby forming an extended first end 20 thereof (see FIG. 2). Similarly the second end 22' of the rod shaped member 28 is rigidly fitted into a cap 23, which then forms an extended second end 22 of the rod-shaped member 28. The term rod-shaped member as used herein thus also includes those portions 23, 34 which are fixed at its ends.

It may be noted that the rod-shaped member 28 may also be formed from a single piece, wherein the first end has an increased diameter in order to serve as a portion to be accessed by a receiving part of a bone anchor 30, 32.

An axial dampening element 24 is attached (e.g., press-fitted) to the cap 23 at the second end 22 of the rod-shaped member 28. The axial dampening element is thereby arranged to be slidable along the rod shaped member 28 with its non-fixed portions. In this embodiment, an opening or bore is formed in the axial dampening element 24 such that the rod-shaped member 28 may extend through the dampening element.

As shown in FIGS. 3-5, particularly in the sectional profile of FIG. 5A, the axial dampening element 28 can be in the form of a helical spring element, which includes a rigid first connecting portion 62, a flexible spring portion 64, and a rigid second connecting portion 66. The helical spring element may damp compressive and tensural forces acting on the implant device along its longitudinal axis 9.

The connecting portion 66 is fitted onto the cap 23. The other connecting portion 62 is connected (e.g., press-fitted) onto a coupled end 38 of an adjacent slidable sleeve 26 to be described below. In this specific embodiment, the axial dampening element 24 may resiliently move along the longitudinal axis of the rod at least with portions 62, 64.

All three portions 62, 64, 66 of the axial dampening element 24 are made from a single piece comprising Nitinol, Titanium alloys or another biocompatible metal material. Carbon PEEK or biocompatible polymer materials can also be employed.

It may be noted that other types of dampening devices such as elastomer (i.e., PCU, SIBS) may be used alternatively. The present invention shall not be limited to the specific embodiment of a helical spring. Further, the term "dampening" as used herein includes the mere function of reducing load peaks and maximum impact forces acting on respectively involved parts.

The slidable sleeve 26 is connected to the axial dampening element 24 and has the coupled end 38, which provides the connection, and a free end 36, which is not further connected with other parts except the bone anchor 32, by which the sleeve is to be accessed. The free end 36 is oriented towards the first end 20, 20' of the rod shaped member 28 and the coupled end 36 is oriented towards the second end 22, 22' of the rod-shaped member 28.

The sleeve 26 has an inner bore which may comprise three portions in this embodiment. A first bore portion 54, a second bore portion 56 and a third bore portion 55. The first bore portion 54 is arranged adjacent to the coupled end 38 and has a diameter larger than the outer diameter of the rod-shaped member 28 such as to provide a clearance 541. Similarly, the second bore portion 56 is arranged adjacent to the free end 36 and has a diameter larger than the outer diameter of the rod-shaped member 28 in order to provide a sufficient clearance 561 (see FIGS. 5A and 5B) for the rod-shaped member 28 extending inside this bore portion to bend, shear or twist inside the sleeve. Clearances 541 and 561 may be of equal size.

The third bore portion 55 has a diameter which substantially corresponds to the outer diameter of the rod-shaped member 28. This bore portion 55 thus provides a close contact and guide for the sleeve in order to be slidable along the rod-shaped member 28. In this embodiment, the third bore portion having the narrower diameter as compared with the adjacent first and second bore portions 54, 56 is provided by inserting sleeve-like rod guide 40 into the bore of the sleeve 26, as shown in FIG. 2 and in more detail in FIG. 5B. The sleeve-like rod guide 40 may be formed from, e.g., PEEK material and may be rigidly press-fitted into the sleeve 26. The material is chosen such as to reduce wear between the rod and the sleeve. The rod guide 40 may attain a substantial central position inside the sleeve. In other embodiments (not shown) it may be positioned closer to the coupled end 36 of the sleeve such that the first bore portion 54 may even vanish.

The inner (larger) diameter of the second bore portion 56 is chosen not to exceed a limit value such that the flexible rod in case of flexion or shear may contact the inner wall of the bore. Consequently, flexion and shear of the rod-shaped member are limited within a predetermined range due to the limited clearance 561.

In this specific embodiment, the resultant bore of the sleeve having portions 54, 55, 56 includes a stepped profile. It may be noted that other profiles may be realized as well, such as a conical profile, a smoothly rounded profile, multiple steps etc.

In order to maintain a sufficient guiding performance the third bore portion 55 should have the small diameter constantly over a range 58. The receiving part 48 of the bone anchor 32, which accesses the sleeve 26, may then attain a location of the sleeve close to the third bore portion 55. The lengths of corresponding ranges 60, 58 (FIG. 5) should be selected according to the circumstances. In one example, the length of guiding range 58 amounts to at least half the width of the receiving part. Similarly, the length of the clearance range 60 on the free end side may amount to at least half the width of the receiving part.

Regarding the materials used for sleeve (except the rod guide 40), the same composition as for the axial dampening element may be chosen.

No further connection is provided between the free end 36 of the sleeve 26 and the first end of the rod-shaped member 28 towards which the free end 36 is oriented. Hence, the resiliently supported sleeve is coupled to the rod only via its second end 22, 22'. An end position dampening is realized thereby, since axial dampening element 24 takes over the full task of dampening relative motions of the bone anchors 30, 32. Hence, no additional spring or other dampening means is necessary between the sleeve and the first end 20 provided by rod portion 34. The spring constant, or dampening constant of the axial dampening element 24 is chosen accordingly.

One advantage that arises thereby is, that the number of components can be decreased, and that the mutual distance between two bone anchors can be reduced, which may become a critical factor particularly in the lower lumbar spine.

Instead of a dampening element provided between the sleeve and the first end according to prior art, a space S is arranged between both parts. The length of space S depends on the displacement of the sleeve 26 and the axial dampening element 24 and has a predetermined value in rest position of the device 12.

Figure 6:
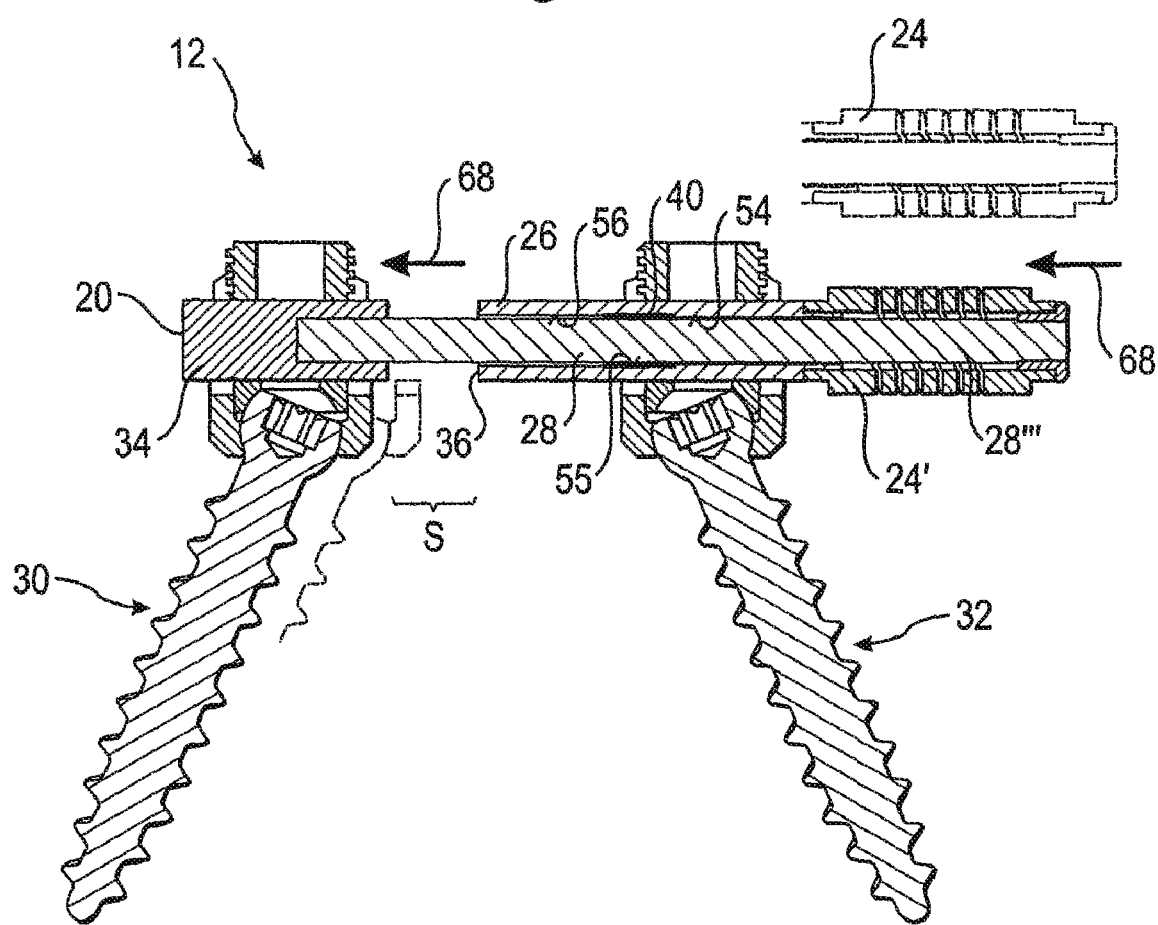
FIG. 6 illustrates in a sectional profile of the bone stabilization device of FIG. 1 the effect of a tensile load acting on the (left side) bone anchor connected to the first end of the rod shaped member.
Figure 7:
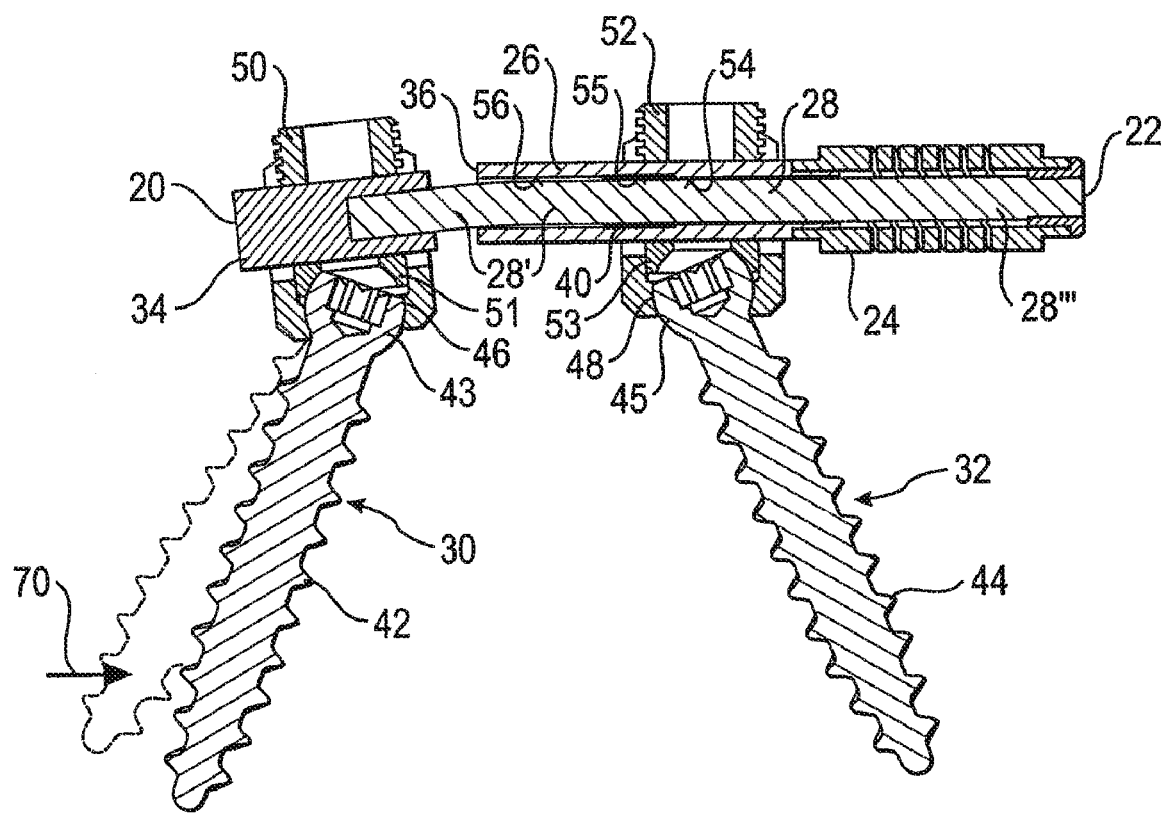
FIG. 7 illustrates in a sectional profile of the bone stabilization device of FIG. 1 the effect of a flexural load acting on the (left side) bone anchor connected to the first end of the rod shaped member.
Figure 8:
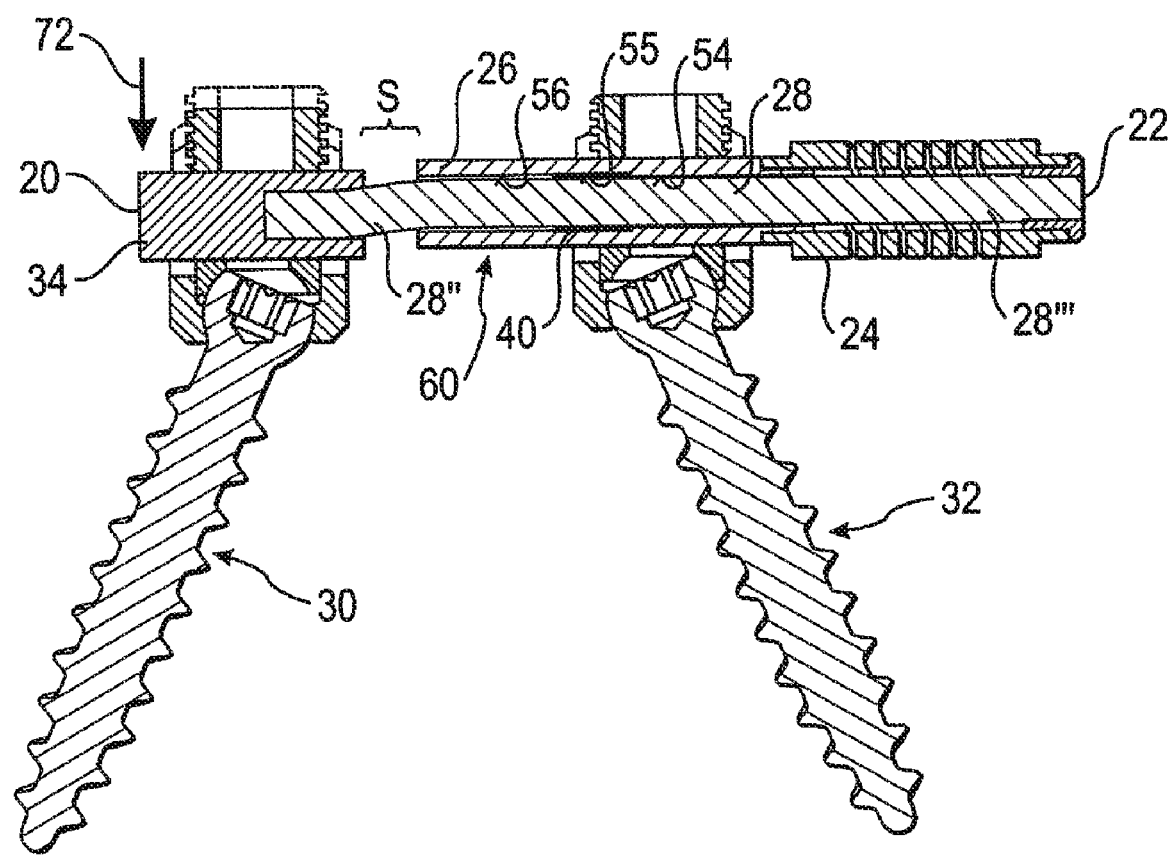
FIG. 8 illustrates in a sectional profile of the bone stabilization device of FIG. 1 the effect of a shear load acting on the (left side) bone anchor connected to the first end of the rod shaped member.

As shown in FIGS. 6-8, the length of space S determines the range in which flexion and shear may occur. FIG. 6 shows the ideal case of axial compression 68 between the two bone anchors 30, 32, FIG. 7 shows the case of flexion 70 and FIG. 8 shows the conventionally most problematic case of a shear movement 72. As can be seen from the Figures, the locations 28', 28" of flexion and shear, respectively, along the rod-shaped member is separated from the corresponding location 28''' where axial dampening occurs.

Hence, the axial dampening element is relieved from bending and shear which increases the lifetime of the dampening element, particularly, e.g., the helical springs used for axial dampening.

The exemplary construction of the bone anchors 30, 32 will now be shortly described. It is noted that, however, that any known bone fastening device other than that shown herein can be used in conjunction with the elongated implant device 10. The bone anchors shown herein may refer to assemblies also known as polyaxial or monoaxial bone anchoring devices, as disclosed, e.g., in EP 1 774 919 A1, by the same applicant. The bone anchors have receiving parts 46, 48 and bone screw 42, 44, respectively. The bone screws include a thread part and a nearly spherical head 43, 45 (shown in FIG. 7), respectively, which is arranged to be rotatable within an opening of the receiving part 46, 48. The rod portion 34 or the sleeve 26 of substantially same outer diameter are received in U-shaped recesses (not shown) of the corresponding receiving part and fixed by set screws 50, 52. Pressure elements 51, 53 serve to transfer the pressure from the rod portion, or sleeve respectively, to the screw head 43, 45, Prior to fixation by the set screws, the bone screws 42, 44 can be oriented within the opening of the receiving part.

Next, a description of a method of assembling the implant device will be given:

At first, a rod-shaped member 28 is formed by providing a thin flexible Nitinol wire and attaching at a first end the rod portion 34 having the bore 35. The connection may be established by press-fitting the rod-shaped member into the bore while applying heat to the parts. Further, the sleeve 26 is fitted into one end of the axial dampening element 24 and the cap 23 is fitted into the other end of the axial dampening element 24. For this purpose, one or both of the sleeve 26 (at the coupled end) and the cap 23 may have a cylindrical ring-like protrusion which fits into the connecting portions of the axial dampening element.

Then, the rod-shaped member 28 is inserted—starting with its second end 22' opposite to the rod portion 34—into the bore portion at the free end 36 of assembled sleeve. The end 22' is afterwards lead through the bore of the sleeve and the dampening element 24. The bore of the cap 23 has a slightly smaller diameter than the outer diameter of the rod-shaped member 28 (the wire). Hence, the cap is then press-fitted onto the second end 22' to provide a rigid durable connection.

The invention has been described with to one specific embodiment. However, the person skilled in the art will readily recognize that several modifications may be applied without departing from the scope described in the claims.

For example, the embodiment described above include first and second portions (i.e., clearances) and a third (guiding) bore portion of the sleeve. However, a bore having one constant diameter throughout its length may also be employed. Moreover, a clearance bore portion may also be formed at the first end of the rod shaped member 28, namely near the opening of the bore 35 of the rod portion 34. The goal of increasing the space in which the rod may shear or bend is then similarly achieved as in the above embodiment. Further, a clearance bore portion may also be formed on both sides of the space S, i.e., at the rod portion 34 and the sleeve 26.

Further, the bone anchors have been described above with regard to polyaxial bone screws. However, the present implant device may also be implemented with monoaxial bone screws, wherein the bone screw and the receiving part for the rod are a single piece or separate pieces.

Further, it has been shown in the embodiment that the sleeve is of cylindrical form and fully encloses the rod. However, it is also possible that the sleeve has other outer cross sectional profiles and/or is provided with slits or the inner bore is open over its entire length.

Still further, the bone stabilization device has been shown to include two bone anchors. However, it is also possible that three or more bone anchors are connected by an implant device according to the invention. For example, a modified version of rod portion 34 is provided as a sleeve, through which the rod shaped member extends towards a further rod portion (not shown) which is to be accessed by a third bone anchor. This modified rod portion 34 or sleeve then need not rigidly fix the rod.

Still further, a third bone anchor may be arranged on the opposite side of the first bone anchor. A symmetrical arrangement is achieved when the mutual movement of the first and third bone anchors is similarly controlled by an axial dampening element located beyond the inner instance range between the two anchors, i.e., a second end position dampening is realized within the same assembly.

What is claimed is:

1. An elongated implant device for stabilizing the spinal column, the implant device comprising:
    a rod-shaped member having a first end and a second end, the rod-shaped member defining a longitudinal axis of the implant device;
    a rod portion at the first end configured to be connected to a first bone anchor;
    a rigid sleeve configured to be connected to a second bone anchor and configured to slide axially on the rod-shaped member, the sleeve having a free end and a coupled end opposite to the free end along the longitudinal axis;
    an axial dampening element configured to be connected between the coupled end of the sleeve and the second end of the rod-shaped member to dampen movement of the sleeve along the longitudinal axis, wherein the coupled end of the sleeve is closer than the second end of the rod-shaped member to the first end of the rod-shaped member;
    wherein the free end of the sleeve is spaced apart from the rod portion when the axial dampening element is in a neutral position to define a space extending along the longitudinal axis between the free end of the sleeve and the rod portion; and
    wherein the space is entirely without axial dampening structures at any location from the free end of the sleeve to the rod portion.

2. The elongated implant device according to claim 1, wherein the sleeve is coupled to the first end solely via the second end of the rod-shaped member.

3. The elongated implant device according to claim 1, wherein the axial dampening element includes a helical spring portion arranged between two rigid connecting portions.

4. The elongated implant device according to claim 1, wherein the rod-shaped member includes a flexible core configured to provide at least one of bending, shearing and torsional flexibility to the rod-shaped member.

5. The elongated implant device according to claim 4, wherein the sleeve has an inner bore including a guiding portion having an inner diameter, the inner diameter corresponding to an outer diameter of the flexible core of the rod-shaped member for supporting and guiding the sleeve on the flexible core along the longitudinal axis.

6. The elongated implant device according to claim 5, wherein the guiding portion is formed by a sleeve-like rod guide fixed inside the inner bore of the sleeve.

7. The elongated implant device according to claim 5, wherein the inner bore of the sleeve further includes a clearance portion having an inner diameter larger than both the inner diameter of the guiding portion and the outer diameter of the flexible core.

8. The elongated implant device according to claim 7, wherein the clearance portion is oriented towards the free end of the sleeve for providing at least one of a flexural movement and shear of the flexible core between the sleeve and the first end, wherein the at least one of the flexural movement and shear of the flexible core is limited by an inner wall part of the clearance bore portion.

9. The implant device according to claim 1, wherein a cap is provided at the second end and is rigidly coupled to the second end of the rod-shaped member as well as to the axial dampening element.

10. The elongated implant device according to claim 1, wherein an outer diameter of the rod portion is substantially the same as an outer diameter of the sleeve.

11. The elongated implant device according to claim 10, wherein the rod portion includes a bore, wherein a flexible core of the rod-shaped member is rigidly fitted in the bore of the rod portion.

12. The elongated implant device according to claim 1, wherein the space has a minimum length needed to allow for a pre-compressed insertion of the device.

13. The elongated implant device according to claim 1, wherein the axial dampening element is the only element capable of dampening a relative movement between the sleeve and the first end along the longitudinal axis.

14. The elongated implant device according to claim 1, wherein the coupled end of the sleeve is configured to slide on the rod-shaped member.

15. The elongated implant device according to claim 1, wherein there is no threaded connection between the sleeve and the rod-shaped member.

16. The elongated implant device according to claim 1, wherein the axial dampening element is coupled to the sleeve on a side of the sleeve opposite a side facing the rod portion.

17. The elongated implant device according to claim 1, wherein the sleeve is axially slidable on the rod-shaped member while maintaining a constant rotatable position relative to the rod-shaped member.

18. The elongated implant device according to claim 1, wherein a portion of the sleeve that is closer to the free end than to the coupled end has a same outer width as an outer width of the rod portion.

19. The elongated implant device according to claim 1, wherein the rod-shaped member extends through a central bore of the axial dampening element.

20. A bone stabilization device for stabilizing the spinal column comprising:
    a first bone anchor;
    a second bone anchor; and
    an elongated implant device comprising:
        a rod-shaped member having a first end including a rod portion configured to be connected to one of the first or second bone anchors and a second end, the rod-shaped member defining a longitudinal axis of the implant device;
        a sleeve configured to be connected to the other one of the first or second bone anchors and slidably arranged on the rod-shaped member, the sleeve having a free end and a coupled end opposite to the free end along the longitudinal axis;
        an axial dampening element configured to be connected to the coupled end of the sleeve and located between the coupled end of the sleeve and the second end of the rod-shaped member to dampen movement of the sleeve along the longitudinal axis;
        wherein the free end of the sleeve is spaced apart axially from the rod portion when the axial dampening element is in a neutral position to define a space extending along the longitudinal axis between the free end of the sleeve and the rod portion; and
    wherein when the first bone anchor and the second bone anchor are respectively connected to the rod-shaped member and the sleeve, the elongated implant device is entirely without axial dampening structures at any location from the first bone anchor to the second bone anchor.

21. The bone stabilization device according to claim 20, wherein at least one of the first and second bone anchors includes:
    a receiving part for receiving the sleeve, the rod portion or the first end of the implant device, respectively;

a bone screw for fastening the receiving part to an adjacent bone, the bone screw having a first end configured to be attached to the bone and a second end configured to be held within the receiving part;

a fixation element for fixing the sleeve, rod portion or first end within the receiving part; and wherein the second end is arranged within the receiving part to be movable in multiple directions at least prior to final fixation by a fixation element.

22. A method of stabilizing the spinal column with a bone stabilization device comprising a first bone anchor, a second bone anchor, and an elongated implant device comprising a rod-shaped member having a first end including a rod portion and a second end, the rod-shaped member defining a longitudinal axis of the implant device, a sleeve slidably arranged on the rod-shaped member, the sleeve having a free end and a coupled end opposite to the free end along the longitudinal axis, an axial dampening element configured to be connected to the coupled end of the sleeve and located between the coupled end of the sleeve and the second end of the rod-shaped member to dampen movement of the sleeve along the longitudinal axis, wherein the free end of the sleeve is spaced apart axially from the rod portion when the axial dampening element is in a neutral position to define a space extending along the longitudinal axis between the free end of the sleeve and the rod portion, the method comprising:

attaching the first bone anchor to a bone or vertebrae;

attaching the second bone anchor to another bone or vertebrae;

connecting the rod portion to the first bone anchor; and connecting the sleeve to the second bone anchor, such that the elongated implant device is entirely without axial dampening structures at any location from the first bone anchor to the second bone anchor.

* * * * *